(12) United States Patent
Ma et al.

(10) Patent No.: US 11,297,923 B2
(45) Date of Patent: Apr. 12, 2022

(54) APPLYING METHOD AND SYSTEM OF NAIL POLISH

(71) Applicants: Carol Ma, Hacienda Heights, CA (US); Wan Jou Chen, Rowland Heights, CA (US)

(72) Inventors: Carol Ma, Hacienda Heights, CA (US); Wan Jou Chen, Rowland Heights, CA (US)

( * ) Notice: Subject to any disclaimer, the term of this patent is extended or adjusted under 35 U.S.C. 154(b) by 374 days.

(21) Appl. No.: 16/194,378

(22) Filed: Nov. 18, 2018

(65) Prior Publication Data
US 2020/0154849 A1 May 21, 2020

(51) Int. Cl.
| A45D 34/04 | (2006.01) |
| A45D 29/00 | (2006.01) |
| B05B 7/24 | (2006.01) |
| A61K 8/81 | (2006.01) |
| A61K 8/37 | (2006.01) |
| A61K 8/35 | (2006.01) |
| A61Q 3/02 | (2006.01) |
| A61K 8/55 | (2006.01) |
| A45D 34/00 | (2006.01) |
| A45D 31/00 | (2006.01) |

(52) U.S. Cl.
CPC ........... *A45D 34/04* (2013.01); *A45D 29/004* (2013.01); *A61K 8/35* (2013.01); *A61K 8/37* (2013.01); *A61K 8/55* (2013.01); *A61K 8/8152* (2013.01); *A61Q 3/02* (2013.01); *B05B 7/2405* (2013.01); *A45D 31/00* (2013.01); *A45D 2034/002* (2013.01); *A45D 2034/005* (2013.01); *A61K 2800/43* (2013.01); *A61K 2800/87* (2013.01)

(58) Field of Classification Search
CPC .... A45D 44/005; A45D 34/04; A45D 29/004; A45D 31/00; A45D 2034/002; A45D 2034/005; A45D 2029/005; A45D 29/18; A45D 2200/057; A45D 2300/10; A61K 8/35; A61K 8/37; A61K 8/55; A61K 8/8152; A61Q 3/02; B05B 7/2405; B05B 7/2408; B05B 7/2416
See application file for complete search history.

(56) References Cited

U.S. PATENT DOCUMENTS

| 2,234,657 | A | * | 3/1941 | Smaldone | A45D 29/001 132/285 |
| 2,262,977 | A | * | 11/1941 | Vasil | A45D 29/004 132/285 |
| 2,283,703 | A | * | 5/1942 | Stedman | A45D 29/004 132/285 |
| 3,515,154 | A | * | 6/1970 | La Morgese | B65D 83/40 132/73.5 |

(Continued)

*Primary Examiner* — Nicholas D Lucchesi
(74) *Attorney, Agent, or Firm* — Pillsbury Winthrop Shaw Pittman LLP

(57) ABSTRACT

An applying method of a nail polish on a nail surface via an airbrush applicator, including the steps of: filling a predetermined amount of nail polish in a polish container of the airbrush applicator; actuating an air compressor of the airbrush applicator, which is powered by a rechargeable battery thereof, for generating pressurized air; controlling a flow of the pressurized air to mix with the nail polish so as to form an aerosol on the nail surface; and drying the nail polish on the nail surface to form a nail coating thereon.

35 Claims, 4 Drawing Sheets

(56) References Cited

U.S. PATENT DOCUMENTS

| | | | | |
|---|---|---|---|---|
| 4,577,648 A * | 3/1986 | Dinerstein | ............. | A45D 29/00 132/73 |
| 5,150,726 A * | 9/1992 | Rucker | ................. | A45D 29/004 132/285 |
| 5,248,096 A * | 9/1993 | Hoey | .................... | B05B 7/2481 239/104 |
| 5,427,121 A * | 6/1995 | Polito | .................. | A45D 29/004 132/200 |
| 5,454,517 A * | 10/1995 | Naemura | .............. | B05B 1/3046 239/390 |
| 5,873,375 A * | 2/1999 | Johnson | ................ | A45D 29/004 132/200 |
| 5,996,591 A * | 12/1999 | Landa | .................. | A45D 34/042 132/200 |
| 6,213,131 B1 * | 4/2001 | Vien | ..................... | A45D 29/004 132/285 |
| 6,626,183 B1 * | 9/2003 | Pietrocola | ............ | A45D 29/001 132/73 |
| 7,798,061 B2 * | 9/2010 | Dilou | .................. | A45D 29/004 101/127.1 |
| 8,474,464 B2 * | 7/2013 | Smith | .................. | A45D 34/042 132/200 |
| 9,545,643 B2 * | 1/2017 | Thompson | ............ | B05B 9/0416 |
| 9,597,702 B1 * | 3/2017 | Ciervo | .................. | B05B 7/2478 |
| 10,390,601 B2 * | 8/2019 | Mehta | .................. | A45D 44/005 |
| 2003/0073753 A1 * | 4/2003 | Lilley | .................. | A61K 8/8152 522/18 |
| 2004/0069869 A1 * | 4/2004 | Ptak | ....................... | B05B 7/2416 239/398 |
| 2004/0173232 A1 * | 9/2004 | Chang | .................... | A45D 31/00 132/73 |
| 2004/0217198 A1 * | 11/2004 | Lloyd | .................. | B05B 7/2421 239/306 |
| 2005/0016448 A1 * | 1/2005 | Dilou | .................. | A45D 29/004 118/301 |
| 2005/0166940 A1 * | 8/2005 | South-Mitchell | .... | A45D 29/004 132/285 |
| 2006/0180496 A1 * | 8/2006 | Miner | .................. | B44D 2/002 206/581 |
| 2007/0011836 A1 * | 1/2007 | Brewer | .............. | A61C 17/3481 15/220.1 |
| 2008/0092914 A1 * | 4/2008 | Baxter | .................. | A45D 34/04 132/200 |
| 2010/0116284 A1 * | 5/2010 | Smith | .................. | A45D 29/00 132/200 |
| 2013/0068858 A1 * | 3/2013 | Nuzzo | .................. | B05B 7/2478 239/375 |
| 2015/0235402 A1 * | 8/2015 | Anderson | ........... | G06F 3/04845 345/641 |
| 2015/0366318 A1 * | 12/2015 | Kim | ....................... | A45D 31/00 132/73 |
| 2018/0000230 A1 * | 1/2018 | Streeter | .................... | A61Q 3/02 |
| 2019/0314997 A1 * | 10/2019 | Amundson | ........... | A45D 40/30 |
| 2020/0360956 A1 * | 11/2020 | Santana | ................ | A45D 44/00 |

\* cited by examiner

APPLYING METHOD AND SYSTEM OF NAIL POLISH

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to cosmetic applicators, and more particularly to an applying method and system of a nail polish, which can evenly apply a nail coating on a user's fingernail or toenails while being time effective.

Description of Related Arts

Various methods have been devised to alleviate the burden on individuals applying nail polish to their fingernail or toenails. A conventional method is to apply the nail polish on the nail surface via a brush. However, such conventional method has several drawbacks of unevenly nail coating on the nail surface and misapplying the nail polish on the cuticle. In addition, it is a material waste of the thicken nail coating applied by the brush and it is a time consuming to dry the thicken nail coating on the nail surface. In other words, it is difficult for a user to paint the nail polish neatly by herself unless it is done by cosmetic professionals.

Airbrushes are also used to paint or apply an acrylic coating on the nail surface as an alternative method. The advantages of using airbrush method are forming a thin and even acrylic coating on the nail surface and rapidly air-drying the acrylic coating thereon. However, the airbrush method requires complicated system which comprises an independent air compressor station electrically connected to a power plug and an air sprayer connected thereto via an air tube. The pressurized air generated by the air compressor station is guided to flow to the air sprayer via the air tube and is mixed with a kind of acrylic pigment polish at the air sprayer to form an aerosol so as to spray on the nail surface. Accordingly, the airbrush system is bulky and is not considered as a home appliance or portable appliance. In addition, the acrylic pigment polish which generally does adverse effect to the human nail may also be accidentally sprayed on the cuticle via the air sprayer. The air sprayer is difficult to control the pressuring level of the pressurized air in order to control the amount of acrylic pigment polish being sprayed on the nail surface. Furthermore, the maintenance of the airbrush system is not easy for the user such as cleaning the air sprayer and maintaining the optimal working condition of the air compressor station. As a result, the airbrush method is usually available commercially and is operated by professional salons.

SUMMARY OF THE PRESENT INVENTION

The invention is advantageous in that it provides an applying method and system of a nail polish, such as a gel polish, that can evenly apply a nail coating on a user's fingernail or toenails while being time effective.

Another advantage of the invention is to provide a nail polish applying method, wherein the operation is simple, rapid and easy by a single action of the actuating control for controlling a flow of the pressurized air to mix with the nail polish so as to form an aerosol on the nail surface.

Another advantage of the invention is to provide a nail polish applying method, which can apply the nail coating on the nail surface of the artificial nail or the user.

Another advantage of the invention is to provide a nail polish applying system, wherein the airbrush applicator is a hand-held applicator adapted for being held by the operator's hand to enhance the portability of the airbrush applicator.

Another advantage of the invention is to provide a nail polish applying system, wherein the airbrush applicator is equipped with a rechargeable battery to minimize any electrical cable connection of the airbrush applicator during the operation.

Another advantage of the invention is to a nail polish applying kit, wherein all necessary nail polish components are involved for completing the nail polish operation.

Another advantage of the invention is to provide a nail polish applying method and system, wherein no expensive or complicated structure is required to employ in the present invention in order to achieve the above mentioned objects. Therefore, the present invention successfully provides an economic and efficient solution for easily and rapidly applying the nail coating on nail surface.

Additional advantages and features of the invention will become apparent from the description which follows, and may be realized by means of the instrumentalities and combinations particular point out in the appended claims.

According to the present invention, the foregoing and other objects and advantages are attained by an applying method of a nail polish on a nail surface via an airbrush applicator, comprising the following steps.

(A) Fill a predetermined amount of nail polish in a polish container of the airbrush applicator.

(B) Actuate an air compressor of the airbrush applicator, which is powered by a rechargeable battery thereof, for generating pressurized air.

(C) Control a flow of the pressurized air to mix with the nail polish so as to form an aerosol on the nail surface.

(D) Dry the nail polish on the nail surface to form a nail coating thereon.

In accordance with another aspect of the invention, the present invention comprises a nail polish applying system, comprising an airbrush applicator for applying a nail polish on a nail surface. The airbrush applicator comprises:

a handle frame adapted for being held by an operator's hand;

a polish container supported by the handle frame for containing a predetermined amount of nail polish therein;

a power assembly which comprises an rechargeable battery received in the handle frame, and an air compressor powered by the rechargeable battery for generating pressurized air; and a controlling assembly which comprises an actuating control operatively connected to the air compressor for controlling a flow of the pressurized air to mix with the nail polish so as to form an aerosol, and a nozzle head extended communicating with the air compressor and the polish container for applying the aerosol on the nail surface so as to form a nail coating thereon once the nail polish is dried.

In one embodiment, the nail polish is preferred to be a gel polish which comprises a composition of a 20-30% by weight of acrylates copolymer, a 5-15% by weight of hydroxyethyl methacrylate, a 1 to 3% by weight of trimethylbenzoyl diphenylphosphine oxide, a 30-40% by weight of acetone, and a 30-40% by weight of ethyl acetate.

In one embodiment, the composition of the nail polish may further comprises a 3% or less by weight of MICK, a 3% or less by weight of titanium dioxide, a 3% or less by weight of pigment red, and a 3% or less by weight of carbon black.

In accordance with another aspect of the invention, the present invention comprises a plurality of nail polishes in different colors, an airbrush applicator, and a nail protection bottle.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 1:
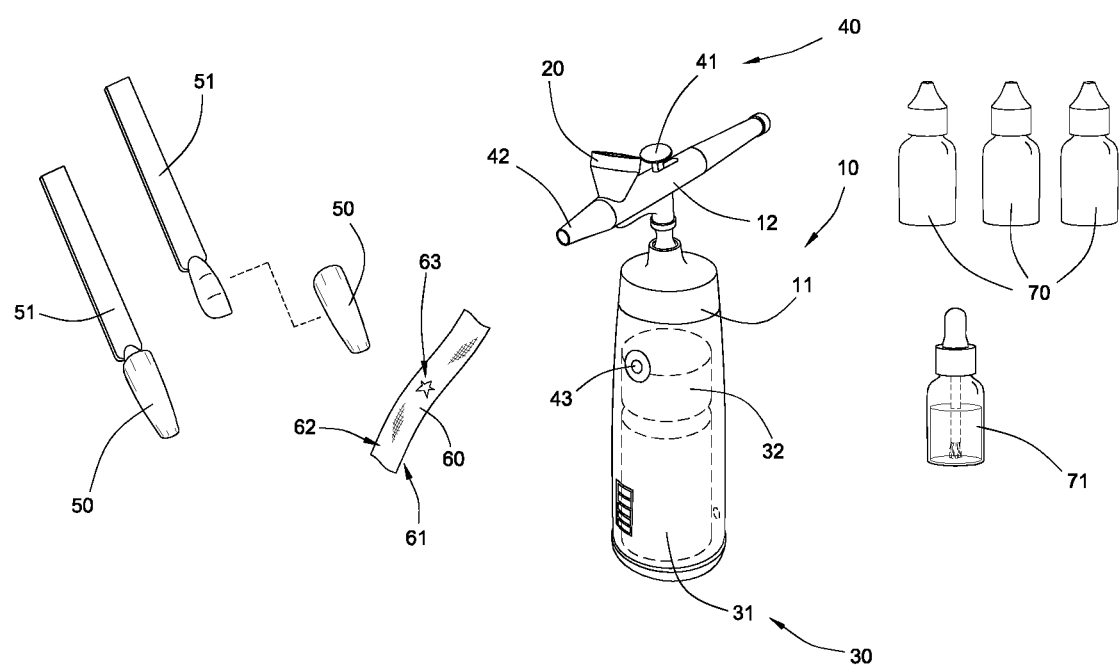
FIG. 1 is a perspective view of a nail polish applying kit according to a preferred embodiment of the present invention.
Figure 2:
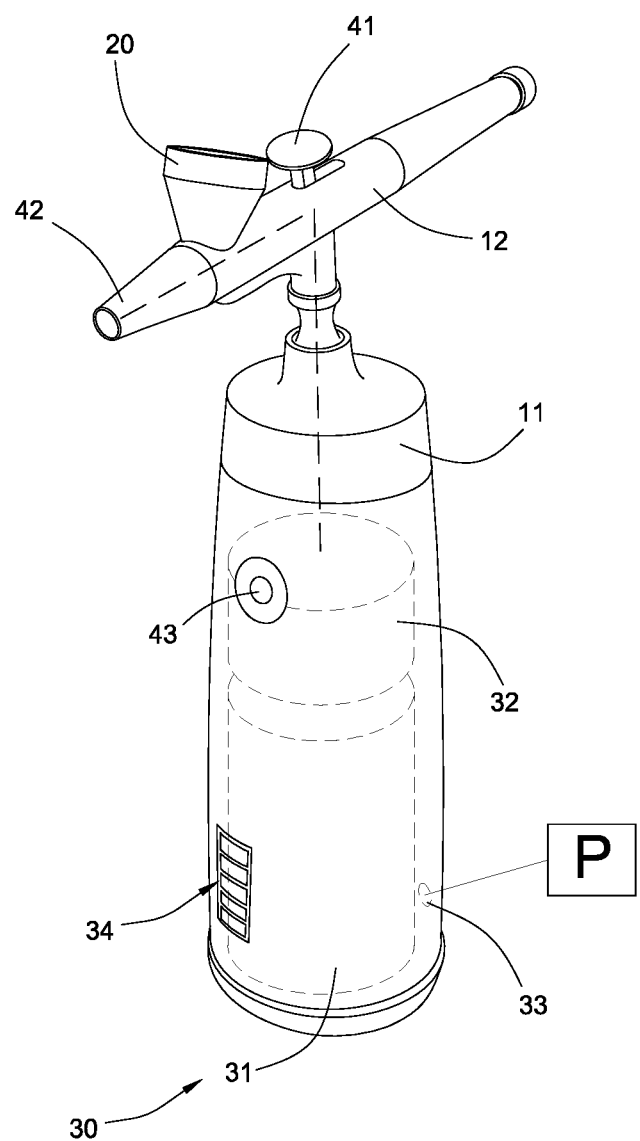
FIG. 2 is a perspective view of an airbrush applicator according to the above preferred embodiment of the present invention.

Referring to FIGS. 1 and 2 of the drawings, a nail polish applying system according to a preferred embodiment of the present invention is illustrated, wherein the airbrush applicator for applying a nail polish on a nail surface. According to the preferred embodiment, the airbrush applicator, which is a hand-held applicator, comprises a handle frame 10, a polish container 20, a power assembly 30, and a controlling assembly 40.

According to the preferred embodiment, the nail polish to be applied by the nail polish applying system is preferred to be a gel polish which is a composition including a 20-30% by weight of acrylates copolymer, a 5-15% by weight of hydroxyethyl methacrylate, a 1 to 3% by weight of trimethylbenzoyl diphenylphosphine oxide, a 30-40% by weight of acetone, and a 30-40% by weight of ethyl acetate.

Furthermore, the composition of the nail polish may further comprises a 3% or less by weight of MICK, a 3% or less by weight of titanium dioxide, a 3% or less by weight of pigment red, and/or a 3% or less by weight of carbon black.

As shown in FIG. 2, the handle frame 10, which is adapted for being held by an operator's hand, comprises a handle grip 11 being gripped by the operator's hand, and a nozzle support 12 extended from the handle grip 11. The polish container 20 is supported by the handle frame 10 for containing a predetermined amount of nail polish therein. Accordingly, the polish container 20 comprises a funnel upwardly extended from the nozzle support 12, wherein the operator is able to fill the nail polish in the polish container 20.

The power assembly 30 comprises a rechargeable battery 31 received in the handle frame 10, and an air compressor 32 powered by the rechargeable battery for generating pressurized air. Accordingly, the rechargeable battery 31 and the air compressor 32 are supported in the handle grip 11 at a position that the air compressor 32 is located above the rechargeable battery 31.

The power assembly 30 further comprises a charging terminal 33 formed at the handle grip 11 of the handle frame 10 to electrically link to the rechargeable battery 31, and a battery indicator 34 electrically linked to the rechargeable battery 31 for indicating an electrical level thereof. Therefore, the operation of the airbrush applicator, the air compressor 32 is directly powered by the rechargeable battery 31, wherein no electric cable is required for electrically connecting to the rechargeable battery 31.

The controlling assembly 40 comprises an actuating control 41 operatively connected to the air compressor 32 for controlling a flow of the pressurized air to mix with the nail polish so as to form an aerosol, and a nozzle head 42 extended communicating with the air compressor 32 and the polish container 20 for applying the aerosol on the nail surface so as to form a nail coating thereon once the nail polish is dried.

The actuating control 41 is a pressure control movably coupled at nozzle support 12 to actuate the air compressor 32 when the actuating control 41 is pressed. Accordingly, when the actuating control 41 is pressed slightly, the air compressor 32 is actuated to produce a lower air pressure to mix with the nail polish. When the actuating control 41 is further pressed, the air pressure will be gradually increased, such that the air compressor 32 will produce a higher air pressure to mix with the nail polish. Therefore, the operator is able to control the flow of pressurized air to adjust an amount of nail polish mixing with the pressurized air so as to adjust a thickness of the nail coating on the nail surface.

The nozzle head 42 is coupled at the nozzle support 12, wherein the nozzle head 42 has one channel communicatively extended to the air compressor 32 and another channel communicatively extended to the polish container 20. Therefore, when the pressurized air is guided to flow along the nozzle head 42, the pressurized air is mixed with the nail polish to form the aerosol.

In order to further control the flow of pressurized air, the power assembly 40 further comprises a power control 43 electrically linked to the rechargeable battery 31 to adjustably control a power level of the rechargeable battery 31. Accordingly, the power control 43 is electrically connected to the rechargeable battery 31 to switch on and off the air compressor 32 and to adjust the electrical power to the air compressor 32. In one embodiment, when the power control 43 is pressed once, the rechargeable battery 31 is activated to switch on the air compressor 32 at a high power level. When the power control 43 is pressed again, the rechargeable battery 31 is activated to switch on the air compressor 32 at a low power level from the high power level. When the power control 43 is pressed at the third time, the rechargeable battery 31 is deactivated to switch off the air compressor 32.

Figure 3:
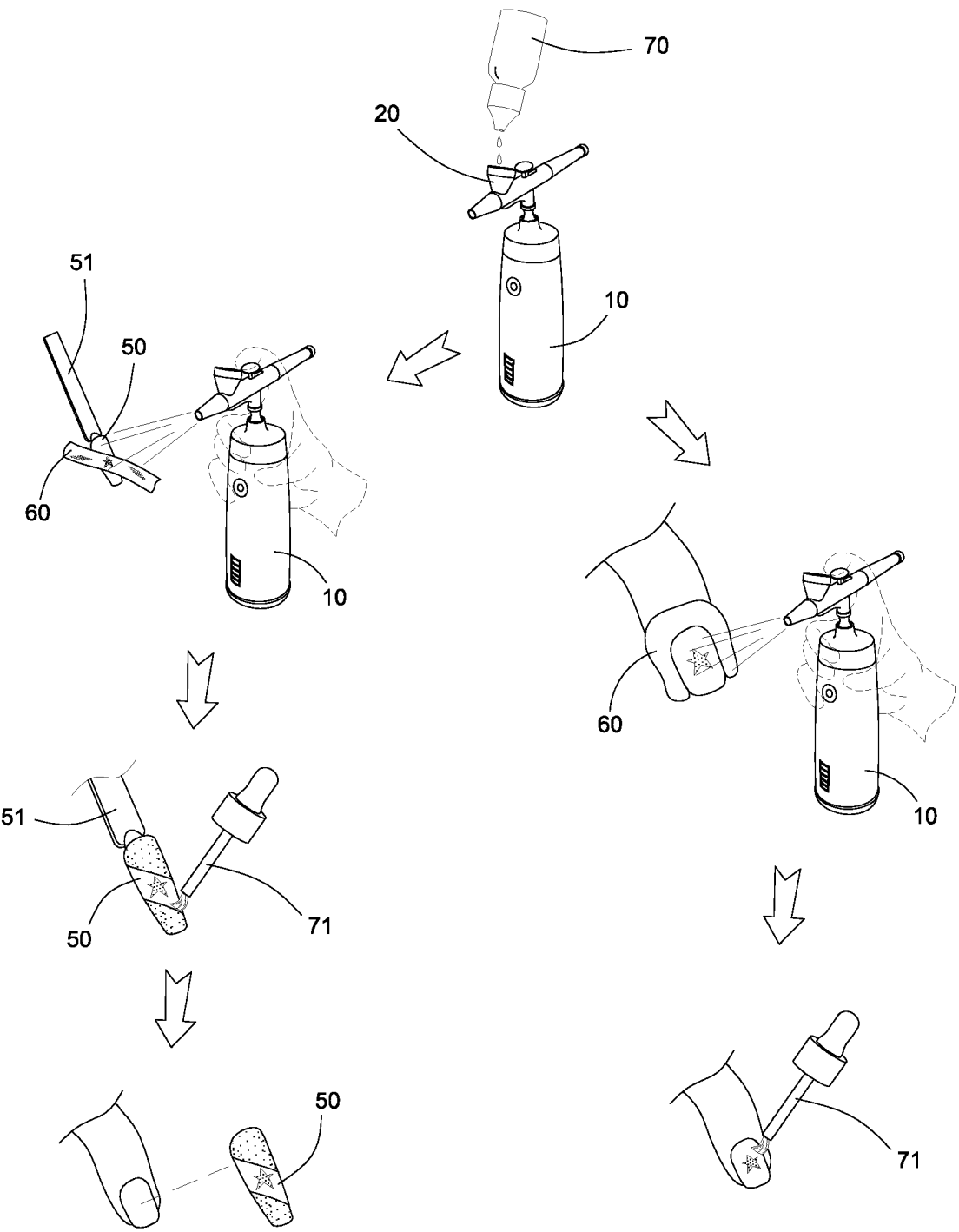
FIG. 3 illustrates the nail polish applying method according to the above preferred embodiment of the present invention.

As shown in FIG. 3, the nail polish applying system further comprises an artificial nail 50 defining the nail surface thereon, and an elongated handling member 51 for holding the artificial nail 50 in position, wherein the artificial nail 50 is adapted for removably attaching on a nail of a user. In other words, the artificial nail has a top side defining the nail surface thereon and a bottom side removably attaching on the nail of the user. Therefore, the nail polish can be pre-coated on the artificial nail 50 before the artificial nail 50 is attached on the user's nail.

The handling member 51 has one end detachably coupling at the bottom side of the artificial nail 50. Therefore, the operator is able to hold the handling member 51 by one hand and to operate the airbrush applicator by another hand to apply the nail polish on the nail surface of the artificial nail 50. Therefore, the nail polish is dried to form the nail coating on the nail surface of the artificial nail 50, the artificial nail 50 is removed from the handling member 51. The artificial nail 50 can be adhered on the nail of the user when the adhesive is applied on the nail of the user.

As shown in FIG. 1, the nail polish applying system further comprises a masking tape 60 for ensuring the nail polish being applied on a desired area of the nail surface. Accordingly, the masking tape 60 comprises a bottom adhering side 61 for removably applying on the nail surface before the aerosol is applied thereon, and a top covering side 62 for covering an unpolished area of the nail surface. The masking tape 60 can be cut or torn in any shape to cover the unpolished or unwanted area of the nail surface. In one embodiment, the masking tape 60 has a customized through slot 63 for allowing the aerosol applied on the nail surface therethrough. For example, the customized through slot 63 has a star shape, such that after the aerosol is applied on the nail surface, the nail coating is formed with the corresponding star shape on the nail surface. Another example illustrates the masking tape 60 has a strip shape to guide the aerosol applied on the nail surface so as to form the strip nail coating on the nail surface.

According to the preferred embodiment, the nail polish can also be directly applied on the nail surface of the user. In one embodiment, the masking tape 60 has a U-shaped configuration removably applied on a cuticle of a user at a border of the nail surface, as shown in FIG. 3. It is worth mentioning that two or more masking tapes 60 can be used at the same time on the nail surface.

As shown in FIG. 1, the present invention further provides a nail polish applying kit which comprises the nail polish applying system with a plurality of bottles of nail polishes 70 and a bottle of protection coating 71. Accordingly, the nail polishes 70 are provided in different colors, wherein the user/operator is able to select one of the nail polishes 70 to be applied on the nail surface. The selected nail polish 70 can be filled in the polish container 20 of the airbrush applicator. Once the nail polish is dried and formed the nail coating on the nail surface, the protection coating 71 can be applied on the nail surface via a nail brush. It is worth mentioning that the bottles of nail polishes 70 and protection coating 71 are UV protection bottles to block the UV light penetrating therethrough. The bottle of protection coating 71 includes the nail brush while the bottles of nail polishes 70 includes a droplet opening for controllably dropping the nail polish into the polish container 20.

Figure 4:
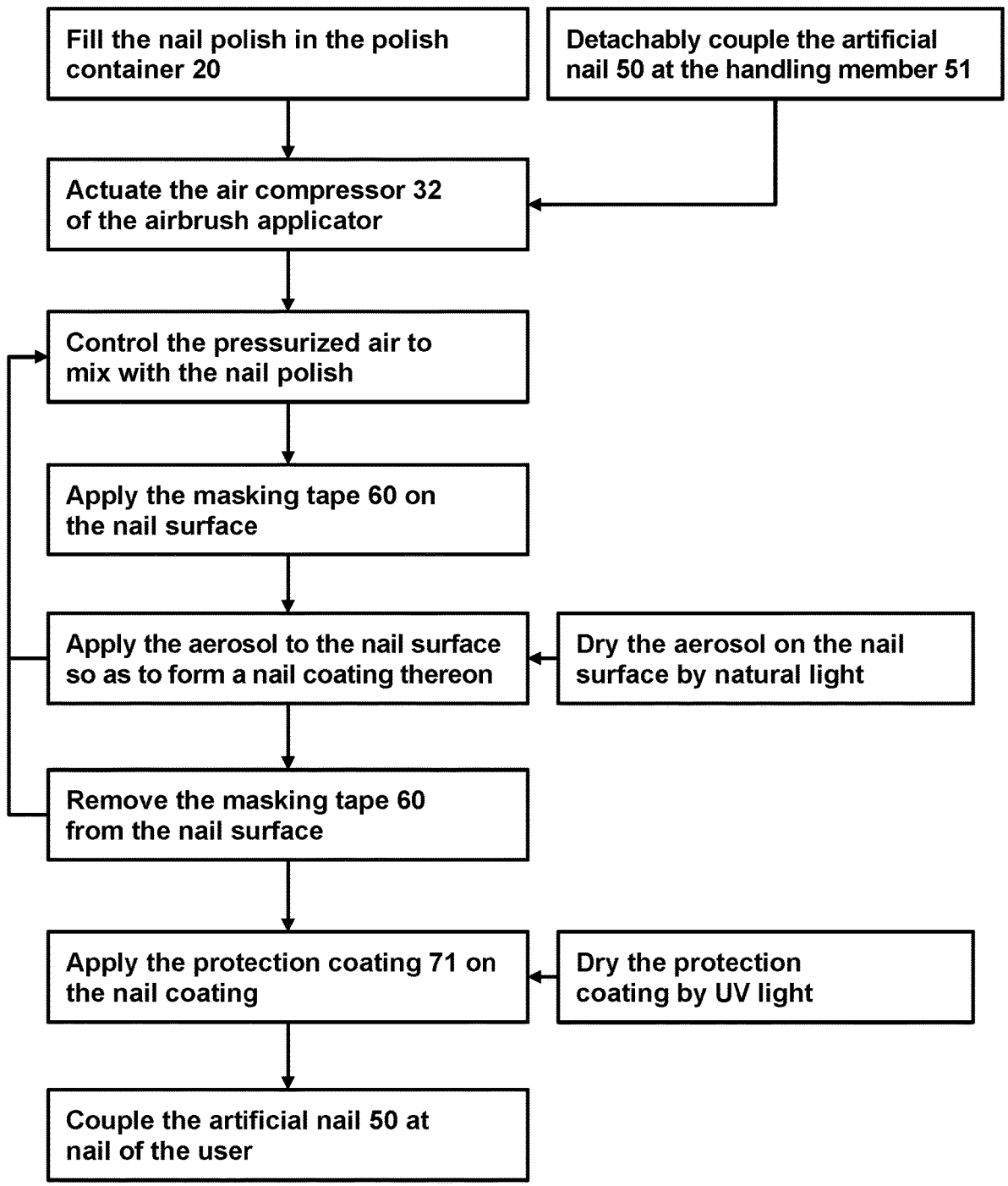
FIG. 4 is a block diagram illustrating the nail polish applying method according to the above preferred embodiment of the present invention.

FIGS. 3 and 4 illustrate an applying method of the nail polish on the nail surface which comprises the following steps.

(1) Fill a predetermined amount of nail polish in the polish container 20 of the airbrush applicator. Accordingly, the selected nail polish is filled in the polish container 20 of the airbrush applicator.

As described above, the nail polish is embodied as a gel polish composition including at least a 20-30% by weight of acrylates copolymer, a 5-15% by weight of hydroxyethyl methacrylate, a 1 to 3% by weight of trimethylbenzoyl diphenylphosphine oxide, a 30-40% by weight of acetone, and a 30-40% by weight of ethyl acetate.

In one embodiment, the composition of the nail polish may further comprises a 3% or less by weight of MICK, a 3% or less by weight of titanium dioxide, a 3% or less by weight of pigment red, and a 3% or less by weight of carbon black.

(2) Actuate the air compressor 32 of the airbrush applicator, which is powered by the rechargeable battery 31 thereof, for generating the pressurized air. It is worth mentioning that the rechargeable battery 31 is ensured for being charged before the operation of the airbrush applicator. The operator is able to switch on the air compressor 32 and to control different power levels of the rechargeable battery 31 by the actuation of power control 43.

(3) Control a flow of the pressurized air to mix with the nail polish so as to form the aerosol on the nail surface. Accordingly, the operator is able to control the pressurized level of the air compressor 32 via the actuating control 41.

(4) Apply the masking tape 60 on the nail surface.

(5) Dry the nail polish on the nail surface to form the nail coating thereon.

(6) Remove the masking tape 60 from the nail surface after the nail coating is formed.

(7) Apply the protection coating 71 on the nail coating. Preferably, the nail polish on the nail surface is dried by exposing the nail polish under natural light and the protection coating 71 is dried by exposing the protective coating 71 under lighting such as LED light or UV light.

Accordingly, the method further comprises a step of repeating the steps (3) and (5) for applying a second nail coating on the nail surface. Accordingly, once the first nail coating is formed on the nail surface, the second nail polish can be applied on the first nail coating and/or the nail surface. In other words, the second nail coating can be overlapped on the first nail coating or can be applied on the unpolished area of the nail surface.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An applying method of a nail polish on a nail surface via a hand-held airbrush applicator, the method comprising the steps of:

(a) filling a predetermined amount of nail polish in a polish container, the polish container comprising a funnel upwardly extended from a nozzle support of the airbrush applicator;

(b) activating a rechargeable battery to control power to an air compressor for generating pressured air, the rechargeable battery and air compressor being supported in a handle grip of the airbrush applicator;

(c) controlling a flow of pressurized air to a nozzle head coupled to the nozzle support by an actuating control operatively connected to the air compressor by a connection within the handle frame, the pressurized air mixing with the nail polish from the polish container to form an aerosol;

(d) applying the aerosol to a nail surface;

(e) drying the nail surface to form a nail coating thereon.

2. The method, as recited in claim 1, further comprising the steps of:

(f) applying a masking tape on the nail surface before the aerosol is applied to the nail surface; and (g) removing said masking tape from the nail surface after the nail coating is formed.

3. The method, as recited in claim 2, wherein the nail coating is formed on said nail surface of an artificial nail to be attached on a nail surface of a user.

4. The method, as recited in claim 3, before the step (b), further comprising a step of detachably coupling said artificial nail at one end of an elongated handling member, wherein said artificial nail is removed from said handling member after said nail coating is dried on said nail surface of said artificial nail.

5. The method, as recited in claim 4, wherein the nail polish is a composition including 20-30% by weight of acrylates copolymer, 5-15% by weight of hydroxyethyl methacrylate, 1 to 3% by weight of trimethylbenzoyl diphenylphosphine oxide, 30-40% by weight of acetone, and 30-40% by weight of ethyl acetate.

6. The method, as recited in claim 5, wherein the composition further includes an additive selected from the group consisting of: 3% or less by weight of MICK, 3% or less by weight of titanium dioxide, 3% or less by weight of pigment red, and 3% or less by weight of carbon black.

7. The method, as recited in claim 3, wherein said masking tape has a customized through slot for allowing the aerosol applied on the nail surface therethrough.

8. The method, as recited in claim 2, wherein said nail surface is a nail surface of a user.

9. The method, as recited in claim 8, wherein said masking tape has a U-shaped configuration removably applied on a cuticle of the user at a border of the nail surface.

10. The method, as recited in claim 1, after the step (e), further comprising a step of repeating the steps (c), (d) and (e) for applying a second nail coating on the nail surface.

11. The method, as recited in claim 1, further comprising a step of applying a protection coating on the nail coating by a nail brush.

12. The method, as recited in claim 11, wherein the nail polish on the nail surface is dried by exposing the nail polish under natural light and said protection coating is dried by exposing said protective coating under UV light.

13. The method, as recited in claim 1, wherein the nail polish is a composition including 20-30% by weight of acrylates copolymer, 5-15% by weight of hydroxyethyl methacrylate, 1 to 3% by weight of trimethylbenzoyl diphenylphosphine oxide, 30-40% by weight of acetone, and 30-40% by weight of ethyl acetate.

14. The method, as recited in claim 13, wherein the composition further includes an additive selected from the group consisting of: 3% or less by weight of MICK, 3% or less by weight of titanium dioxide, 3% or less by weight of pigment red, and 3% or less by weight of carbon black.

15. A hand-held airbrush applicator for applying nail polish to a nail surface, the airbrush applicator comprising:

a handle frame comprising a handle grip adapted for being held by an operator's hand and a nozzle support extending from the handle grip;

a polish container comprising a funnel upwardly extending from the nozzle support for containing a predetermined amount of nail polish therein;

a power assembly supported in the handle grip, the power assembly comprising:

(i) a rechargeable battery; and (ii) an air compressor powered by the rechargeable battery for generating pressurized air;

a controlling assembly comprising:

(i) an actuating control operatively connected to the air compressor by a connection within the handle frame for controlling a flow of pressurized air to mix with the nail polish so as to form an aerosol; and (ii) a nozzle head coupled at the nozzle support, the nozzle head comprising a channel communicatively extended to the air compressor and another channel communicatively extended to the polish container;

wherein the aerosol is applied to a nail surface so as to form a nail coating thereon once the nail polish is dried.

16. The nail polish applying system, as recited in claim 15, further comprising a masking tape, wherein said masking tape comprises a bottom adhering side for removably applying on the nail surface before the aerosol is applied thereon, and a top covering side for covering an unpolished area of the nail surface.

17. The nail polish applying system, as recited in claim 16, further comprising an artificial nail defining the nail surface thereon, wherein said artificial nail is adapted for removably attaching on a nail of a user.

18. The nail polish applying system, as recited in claim 17, further comprising an elongated handling member having one end detachably coupling said artificial nail, wherein said artificial nail is removed from said handling member after said nail coating is dried on said nail surface of said artificial nail.

19. The nail polish applying system, as recited in claim 18, wherein said masking tape has a customized through slot for allowing the aerosol applied on the nail surface therethrough.

20. The nail polish applying system, as recited in claim 16, wherein said masking tape has a U-shaped configuration adapted to be removably applied on a cuticle of a user at a border of the nail surface.

21. The nail polish applying system, as recited in claim 15, wherein said power assembly further comprises a charging terminal formed at the handle grip, wherein the charging terminal is electrically linked to the rechargeable battery.

22. The nail polish applying system, as recited in claim 15, wherein said power assembly further comprises a battery indicator electrically linked to said rechargeable battery for indicating an electrical level thereof.

23. The nail polish applying system, as recited in claim 15, wherein said power assembly further comprises a power control electrically linked to said rechargeable battery to adjustably control a power level of said rechargeable battery.

24. The nail polish applying system, as recited in claim 15, wherein the nail polish is a composition including 20-30% by weight of acrylates copolymer, 5-15% by weight of hydroxyethyl methacrylate, 1 to 3% by weight of trimethylbenzoyl diphenylphosphine oxide, 30-40% by weight of acetone, and 30-40% by weight of ethyl acetate.

25. The nail polish applying system, as recited in claim 24, wherein the nail polish further includes an additive selected from the group consisting of: 3% or less by weight of MICK, 3% or less by weight of titanium dioxide, 3% or less by weight of pigment red, and 3% or less by weight of carbon black.

26. A nail polish applying kit, the kit comprising:
one or more bottles of nail polish;
a hand-held airbrush applicator for applying nail polish to a nail surface, the airbrush applicator comprising:
a handle frame comprising a handle grip adapted for being held by an operator's hand and a nozzle support extending from the handle grip;
a polish container comprising a funnel upwardly extending from the nozzle support for containing a predetermined amount of nail polish therein;
a power assembly supported in the handle grip, the power assembly comprising:
(i) a rechargeable battery; and
(ii) an air compressor powered by the rechargeable battery for generating pressurized air;
a controlling assembly comprising:
(i) an actuating control operatively connected to the air compressor by a connection within the handle frame for controlling a flow of pressurized air to mix with the nail polish so as to form an aerosol; and
(ii) a nozzle head coupled at the nozzle support, the nozzle head comprising a channel communicatively extended to the air compressor and another channel communicatively extended to the polish container;
wherein the aerosol is applied to a nail surface so as to form a nail coating thereon once the nail polish is dried; and
a nail protection bottle containing protection coating and comprising a nail brush for applying said protection coating on the nail coating.

27. The nail polish applying kit, as recited in claim 26, wherein each of the one or more bottles of nail polish contains a composition including 20-30% by weight of acrylates copolymer, 5-15% by weight of hydroxyethyl methacrylate, 1 to 3% by weight of trimethylbenzoyl diphenylphosphine oxide, 30-40% by weight of acetone, and 30-40% by weight of ethyl acetate.

28. The nail polish applying kit, as recited in claim 27, wherein the composition further includes an additive selected from the group consisting of: 3% or less by weight of MICK, 3% or less by weight of titanium dioxide, 3% or less by weight of pigment red, and 3% or less by weight of carbon black.

29. The nail polish applying kit, as recited in claim 26, further comprising a masking tape having a bottom adhering side for removably applying on the nail surface before the aerosol is applied thereon, and a top covering side for covering an unpolished area of the nail surface.

30. The nail polish applying kit, as recited in claim 29, further comprising an artificial nail defining the nail surface thereon, wherein said artificial nail is adapted for removably attaching on a nail of a user.

31. The nail polish applying kit, as recited in claim 30, further comprising an elongated handling member having one end detachably coupling said artificial nail, wherein said artificial nail is removed from said handling member after said nail coating is dried on said nail surface of said artificial nail.

32. The nail polish applying kit, as recited in claim 31, wherein said masking tape has a customized through slot for allowing the aerosol applied on the nail surface therethrough.

33. The nail polish applying kit, as recited in claim 32, wherein each of the one or more bottles of nail polish contains a composition including 20-30% by weight of acrylates copolymer, 5-15% by weight of hydroxyethyl methacrylate, 1 to 3% by weight of trimethylbenzoyl diphenylphosphine oxide, 30-40% by weight of acetone, and 30-40% by weight of ethyl acetate.

34. The nail polish applying kit, as recited in claim 33, wherein the composition further includes an additive selected from the group consisting of: 3% or less by weight of MICK, 3% or less by weight of titanium dioxide, 3% or less by weight of pigment red, and 3% or less by weight of carbon black.

35. The nail polish applying kit, as recited in claim 29, wherein said masking tape has a U-shaped configuration adapted to be removably applied on a cuticle of a user at a border of the nail surface.

* * * * *